US011579103B2

(12) United States Patent
Lyon et al.

(10) Patent No.: US 11,579,103 B2
(45) Date of Patent: Feb. 14, 2023

(54) GENERATING AND DETERMINING THE PRODUCTS OF PREMIXED COMBUSTION OF SOLID MATERIALS IN A MICROSCALE FIRE CALORIMETER

(71) Applicant: The United States of America, as represented by the Administrator of the Federal Aviation Administration, Atlantic City International Airport, NJ (US)

(72) Inventors: Richard E. Lyon, Galloway, NJ (US); Louise Speitel, Absecon, NJ (US); Richard N. Walters, Egg Harbor City, NJ (US)

(73) Assignee: The United States of America, as represented by the Administrator of the Federal Aviation Administration, Washington, DC (US)

( * ) Notice: Subject to any disclaimer, the term of this patent is extended or adjusted under 35 U.S.C. 154(b) by 374 days.

(21) Appl. No.: 16/840,556

(22) Filed: Apr. 6, 2020

(65) Prior Publication Data

US 2020/0340935 A1 Oct. 29, 2020

Related U.S. Application Data

(60) Provisional application No. 62/838,759, filed on Apr. 25, 2019.

(51) Int. Cl.
*G01N 25/24* (2006.01)
*G01N 33/00* (2006.01)
*G01N 33/22* (2006.01)

(52) U.S. Cl.
CPC ......... *G01N 25/24* (2013.01); *G01N 33/0036* (2013.01); *G01N 33/222* (2013.01)

(58) Field of Classification Search
CPC ............................. G01N 25/24; G01N 33/222
See application file for complete search history.

(56) References Cited

U.S. PATENT DOCUMENTS

| 5,981,290 | A | 11/1999 | Lyon et al. | |
|---|---|---|---|---|
| 6,464,391 | B2 | 10/2002 | Lyon | |
| 2006/0133445 | A1* | 6/2006 | Lyon | G01N 25/50 374/8 |

FOREIGN PATENT DOCUMENTS

| CN | 113406297 A | * | 9/2021 |
|---|---|---|---|
| CN | 114018978 A | * | 2/2022 |

OTHER PUBLICATIONS

Richard E. Lyon, Richard Walters, "A Microscale Combustion Calorimeter," Final Technical Report of the United States Department of Transportation/Federal Aviation Administration (DOT/FAA/AR-01/117), Feb. 2002, 28 pp., U.S.A.

(Continued)

*Primary Examiner* — Christopher Adam Hixson
(74) *Attorney, Agent, or Firm* — Lise A. Rode

(57) ABSTRACT

Embodiments described herein provide for the flameless premixed combustion of the pyrolysis gases of a milligram-sized sample of solid material in a microscale fire calorimeter (MFC) at high temperatures of combustion and under precisely controlled fuel-to-oxygen ratios. The microscale fire calorimeter (MFC) device and techniques set out herein provide for the generation of fuel gases from solids and the mixing of those fuel gases with oxygen under controlled conditions to obtain precise fuel/oxygen ratios during combustion. Combustion is conducted under flameless, premixed conditions in a rapid test that can generate soot and other products of incomplete combustion, which may then be analyzed to determine their type and nature. This allows for microscale, accurate, and convenient techniques for the generation and determination of the type and nature of (Continued)

combustion species produced over the full range of fire stages from early stage (over-ventilated) fires to late-stage (under-ventilated/high-toxicity) fires.

18 Claims, 6 Drawing Sheets

(56) References Cited

OTHER PUBLICATIONS

* Richard E. Lyon, Richard N Walters, Stanislav I. Stoliarov, Natiallia Safronava, "Principles and Practices of Microscale Combustion Calorimetry," Final Technical Report of the United States Department of Transportation/Federal Aviation Administration (DOT/FAA/TC-12/53, R1). Apr. 2013, 95 pp., U.S.A. * Link to report here https://www.fire.tc.faa.gov/pdf/TC-12-53.pdf (Please see accompanying transmittal letter).
Richard N. Walters, Richard E. Lyon, "MicroCalorPhiMeter: Controlled Fuel-Oxygen Ratios in the MCC," Presentation, Center for UMass / Industry Research on Polymers (CUMIRP), May 12, 2015, 13 pp., Amherst, MA., U.S.A.
Richard N. Walters, Louise Speitel , Richard E. Lyon, "Polymer Combustion at Constant Fuel/Oxygen Ratios in the Microscale Combustion Calorimeter," Paper & Presentation, 27th Conference on Flame Retardant Materials (BCC Research), May 24, 2016, 33 pp. (total w/cover sheet), Wellesley, MA.,U.S.A.
Richard N. Walters, Louise Speitel , Richard E. Lyon, "Combustion Products of Polymers at Constant Fuel/Oxygen Ratios," Paper & Presentation, 14th International Conference on Fire Science and Engineering (INTERFLAM), Jul. 5, 2016, 37 pp. (total w/cover sheet), Royal Holloway College-University of London, Egham, England.
Richard N. Walters, Louise Speitel , Richard E. Lyon, "Polymer Combustion Products at Constant Fuel/Oxygen Ratios," Abstract & Presentation, International Confederation for Thermal Analysis and Calorimetry (ICTAC), North American Thermal Analysis Society, Inc., (NATAS), Aug. 15, 2016, 49 pp. (total w/cover sheet), Orlando, FL., U.S.A.
Louise Speitel, Richard N. Walters, Richard E. Lyon, "Toxicity Assessment of Polymers in the Microscale Combustion Calorimeter," Paper & Presentation, 8th Triennial International Fire & Safety Conference, Oct. 25, 2016, 31 pp. (total w/cover sheet), Atlantic City, N.J., U.S.A.
Richard N. Walters, R.E.Lyon, N.Safronava, L.Speitel, H.Guo, "Advances in Microscale Combustion Calorimetry and Application," Abstract & Presentation, 16th Fire Retardant Polymeric Materials (FRPM), Jul. 5, 2017, 31 pp. (total w/cover sheet), Manchester, England.
Rudolphe Sonnier, Gaëlle Dorez, Henri Vahabi, Claire Longuet, Laurent Ferry, "FTIR-PCFC Coupling: A New Method for Studying the Combustion of Polymers," Combustion and Flame, May 2014, pp. 1398-1407, vol. 161—Issue 5, Elsevier//Combustion Institute, U.S.A.

* cited by examiner

GENERATING AND DETERMINING THE PRODUCTS OF PREMIXED COMBUSTION OF SOLID MATERIALS IN A MICROSCALE FIRE CALORIMETER

CROSS-REFERENCE TO RELATED APPLICATIONS

This application claims priority to U.S. Provisional Patent Application No. 62/838,759, filed on Apr. 25, 2019 and entitled "Determining the Products of Premixed Combustion of Solid Materials in a Microscale Fire calorimeter," and which is expressly incorporated by reference herein in its entirety.

TECHNICAL FIELD

The disclosed embodiments relate to the field of calorimeters. More specifically, the embodiments relate to the flameless premixed combustion of solids in a microscale fire calorimeter (MFC) at high temperatures of combustion and under precisely controlled fuel-to-oxygen ratios.

BACKGROUND

Flaming combustion of solid fuels in fires is a diffusion- and kinetically-controlled process. Fuel gases from burning solids diffuse into the flame, mix with oxygen from the air, and react to form combustion products at a rate that is controlled by the flame temperature and the fuel/oxygen ratio. When the amount of oxygen exceeds what is required for complete combustion of the fuel gases (as occurs during the early stages of a fire), the oxidation reactions in the flame proceed rapidly to relatively complete/non-toxic combustion products such as water and carbon dioxide. However, when the available oxygen in the air is insufficient to completely oxidize the fuel gases (as occurs in late stage fires when oxygen has been consumed by the fire) the reactions are slower and combustion is incomplete. As a result of this incomplete combustion, highly toxic and life-threatening combustion products such as carbon monoxide and hydrogen cyanide are produced in the flame and the toxicity of the combustion products increases dramatically as the fire grows and the air becomes depleted of oxygen. These toxic combustion products are considered to be a primary hazard of otherwise survivable fires in confined spaces such as rooms and vehicle compartments. Notably, these toxic combustion products are generated in high yield during the burning of flame retardant plastics such as used in aircraft cabins.

The particular type and amount of combustion products generated depend on the chemical composition of the burning material as well as the equivalence ratio of the combustion process, $\Phi$; that is, the actual fuel-to-oxygen mass ratio relative to the fuel-to-oxygen mass ratio value for complete, or stoichiometric, combustion. As known, if this equivalence ratio is equal to one, the combustion is stoichiometric. If $\Phi<1$, the combustion includes excess oxygen, and if $\Phi>1$, the combustion is fuel-rich with incomplete combustion and combustion products.

Currently, the generation and measurement of the combustion products of fuels at well-defined constant equivalence ratios $\Phi$ is limited to fluids (gases, vapors, and liquids) that can be mixed with oxygen and nitrogen at precise ratios. Methods for measuring the combustion products of solid fuels generated at different stages of a fire, however, are generally imprecise and require kilograms of material and bench- or full-scale test equipment. These methods often attempt to independently control the burning (mass loss) rate of the sample and the mass flow rate of oxygen to the flame to adjust the fuel/oxygen mass ratio relative to the stoichiometric value. In such tests, the reported equivalence ratio is a global value for the entire apparatus (GER), because the local fuel/oxygen ratio in the combustion zone (flame) is unknown. Thus, the combustion products generated by the molecular-level processes in the flame at the local $\Phi$ are unknown. Even commercially-available microscale combustion calorimeters (MCC), such as developed by the Federal Aviation Administration, while significantly improving on the aforementioned deficiencies by rapidly providing fundamental thermochemical data and fire performance properties of materials using only milligram-sized solid fuel samples, are also not capable of accurately determining or measuring any of the combustion products except depleted oxygen.

Techniques for generating and determining the type and nature of combustion products in a diffusion flame over the full range of fire stages (i.e., from early stage (over-ventilated) fires to late-stage (under-ventilated/high-toxicity) fires) would be of great practical value for fire safety research, flame retardant materials' design, and safety regulation, allowing for the measurement of the toxic potency of the smoke from burning materials during fires.

SUMMARY

A brief summary is provided herein to help enable a basic or general understanding of various aspects of exemplary embodiments that follow in the more detailed description and the accompanying drawings. This summary is not intended as an extensive or exhaustive overview of all contemplated features of the disclosure nor intended to identify key or critical elements of all aspects of the disclosure, but rather to present concepts as a prelude to more detailed description of the various embodiments that follow in the disclosure.

According to one aspect of the subject matter described in this specification, microscale fire calorimeter (MFC) devices and techniques are provided to measure the toxic potency of the smoke from burning materials.

According to another aspect of the subject matter described in this specification, microscale fire calorimeter (MFC) devices and techniques are provided using milligram-sized solid fuel samples, controlled heating, and flameless premixed gas phase combustion at precise fuel/oxygen ratios to generate combustion products of materials over a range of fire stages.

According to a further aspect of the subject matter described in this specification, microscale fire calorimeter (MFC) devices and techniques are provided wherein the premixed combustion of solid materials is dynamically controlled to precise fuel-to-oxygen ratios relative to stoichiometric fuel-to-oxygen ratios at a constant total volumetric flow rate of oxygen and inert purge gas, and the type and amount of combustion product produced at flame-equivalent temperatures and at the precisely-controlled fuel/oxygen ratios can be measured to determine the toxic potency of smoke generated by solids burning under fire-like conditions.

According to yet another aspect of the subject matter described in this specification, microscale fire calorimeter (MFC) devices and techniques set out herein improve on known combustion calorimeter devices and methods that measure combustion products of solids under controlled fuel/oxygen mass ratios. The microscale fire calorimeter (MFC) devices and techniques set out herein generate fuel gases from milligram-sized samples of solid materials and then mix those generated fuel gases with oxygen under controlled conditions to obtain precise predetermined constant fuel/oxygen ratios. Combustion is conducted in the gas phase, under flameless (i.e., thermal), premixed (uniform) conditions in a short (e.g., 15-minute) test that can generate gaseous products and soot, which are then analyzed to determine their type, amount and nature. This allows for a microscale, accurate, and convenient generation and determination of the type, nature and amount of combustion products generated in flaming combustion over the full range of fire stages.

In accordance with a further aspect of the subject matter described in this specification, microscale fire calorimeter (MFC) devices and techniques are provided to reproduce the conditions of flaming combustion using a non-flaming, gas phase, thermal combustion process by controlling the fuel-to-oxygen ratio at all times during a test and then combusting the fuel/oxygen mixture at flame temperatures greater than 1200° C. and preferably in the range 1500-1800° C., resulting in the production of soot and other incomplete combustion products for analysis.

According to yet a further aspect of the subject matter described in this specification an MFC device for generating gaseous and solid combustion products from burning solids under pre-selected fire-like conditions is provided. The resulting gas yields can be input into toxicity models (e.g., incapacitation, lethality, subacute effects) for each fire-like condition. The MFC device may include a pyrolyzer for thermally decomposing a milligram-sized sample of a solid material under anaerobic conditions to generate fuel gases, the pyrolyzer further including an inlet for receiving a purge gas and a mass flow controller for controlling the mass flow rate of the purge gas through the purge gas inlet into the pyrolyzer; a mixing portion for generating a premixed volume of the generated fuel gases and oxygen at a constant total volumetric flow rate of inert purge gas and oxygen, the mixing portion including an inlet for receiving oxygen and a mass flow controller for controlling the volumetric flow rate of the oxygen through the oxygen inlet into the mixing portion; an ultra-high temperature combustion furnace for combusting the premixed volume of the generated fuel gases and oxygen at the range of flame temperatures in order to produce gaseous and solid combustion products; and, means for controlling the purge gas mass flow controller and the oxygen mass flow controller so that the oxygen-to-fuel mass ratio, $r(T)$, in the ultra-high temperature combustion furnace at a temperature, $T_c$, is a multiplier (i.e., fraction or multiple) of $r_0(T)$, wherein $r_0(T)$ is the stoichiometric oxygen-to-fuel mass ratio for complete combustion of the gaseous products generated by the thermally decomposing solid at each temperature, $T$, during the constant rate of temperature rise of the pyrolyzer.

It will be understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

In order that features of the present disclosure can be understood in detail, a more particular description may be had by reference to aspects and features, some of which are illustrated in the appended drawings. It is to be noted, however, that the drawings illustrate only certain typical aspects and features of this disclosure and are therefore not to be considered limiting of its scope, and that the description may allow for other equally effective aspects and features. The same reference numbers in different drawings may identify the same or similar elements.

No language in the specification should be construed as indicating any non-claimed element as essential to the practice of the techniques of this disclosure. The terms "a" and "an" are used interchangeably above, and are equivalent to the phrase "one or more" as utilized in the present application. The terms "comprising," "having," "including," and "containing" are to be construed as open-ended terms (i.e., meaning "including, but not limited to,") unless otherwise noted above. The recitation of any ranges of values herein is merely intended to serve as a shorthand technique of referring individually to each separate value falling within the range, unless otherwise indicated herein, and each separate value is incorporated into the specification as if it were individually recited. The use of any and all examples, or example language (e.g., "such as"), provided herein is intended merely to better illuminate the disclosure and does not impose a limitation on the scope of the disclosure unless otherwise claimed. Finally, any papers and publications cited herein are hereby incorporated by reference in their entirety.

Certain exemplary embodiments will now be described to provide an overall understanding of the principles of the structure, function, manufacture, and use of the systems and techniques disclosed herein. Those skilled in the art will understand that the exemplary embodiments specifically described herein and illustrated in the accompanying drawings are non-limiting examples and any embodiment or feature described herein as "exemplary," "example," or "illustrative," is not necessarily to be construed as preferred or advantageous over other embodiments or features. Based on the teachings herein one skilled in the art should appreciate that the scope of the disclosure is intended to cover any aspect disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect or feature disclosed herein may be embodied by one or more elements of a claim.

DETAILED DESCRIPTION

Figure 1:
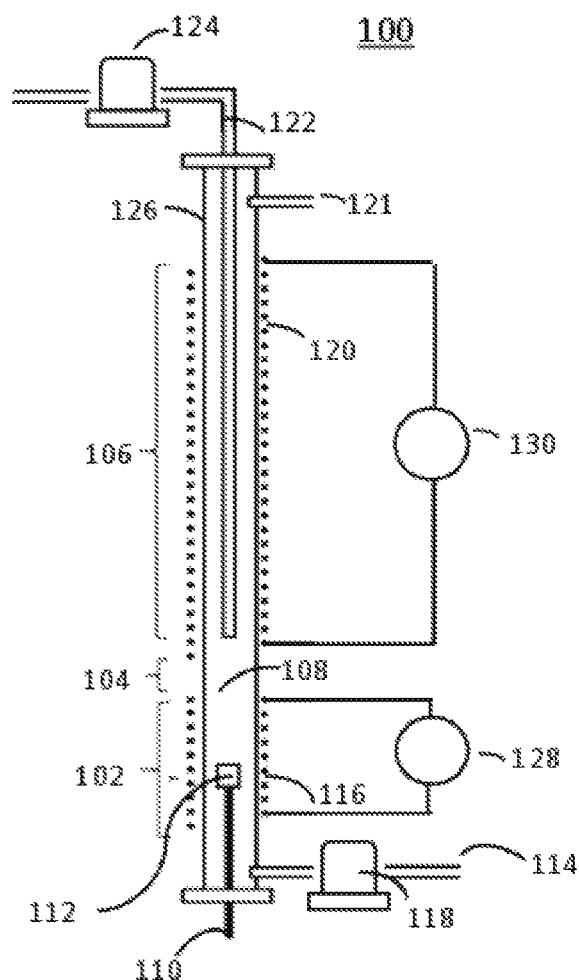
FIG. 1 is a diagram showing aspects and features of a microscale fire calorimeter (MFC) device according to one embodiment.

FIG. 1 shows aspects and features of an embodiment of a microscale fire calorimeter (MFC) 100. In general, MFC 100 uses principles of analytical pyrolysis, combustion gas analysis, and pyrolysis-combustion flow calorimetry (PCFC)) to simulate the flaming combustion of solid materials and fuels. Pyrolysis-combustion flow calorimetry (PCFC) separately reproduces the solid-state and gas phase processes of flaming combustion in a nonflaming test by rapidly controlling the pyrolysis of a solid fuel sample in an inert gas stream in a heated chamber under anaerobic conditions followed by high-temperature oxidation (combustion) of the resulting pyrolyzate in excess oxygen. Current pyrolysis combustion flow calorimeters (PCFC), such as the microscale combustion calorimeter (MCC) developed by the Federal Aviation Administration, may be used to determine heat release capacity and heat release rates as well as other fundamental thermochemical data using only milligram-sized solid fuel samples. However, such PCFC are unable to accurately determine or measure the combustion products of solid materials and fuels at the different stages of a fire including where the solid material is a flame retardant plastic or where combustion is inhibited by flame retardant chemicals added to plastic or other material.

The embodiment of the MFC 100 in FIG. 1 generally includes a pyrolyzer portion 102, a mixing section 104, and a combustion furnace portion 106. Pyrolyzer portion 102 and combustion furnace portion 106 are separately temperature-controllable 128, 130, respectively, by way of interface with a computer system (discussed in more detail with reference to FIGS. 2 and 3 below). Although mixing section 104 and combustion furnace portion 106 are described separately herein, it will be understood that mixing section 104 may be a portion, section, or component of combustion furnace portion 106.

More specifically, and with continuing reference to FIG. 1, pyrolyzer portion 102 of MFC 100 is configured to thermally decompose a small (i.e., milligram-sized) specimen (not shown). Pyrolyzer portion 102 may include a testing chamber 108, in which is preferably disposed a temperature sensor 110 (e.g., a thermocouple) in contact with a sample cup 112 for holding the specimen, and a purge gas inlet 114 that may be used to introduce a constant and continuous flow of an inert gas having negligible effect on combustion (e.g., 99.99% pure $N_2$) for purging the testing chamber 108. A heating member 116 may be used to heat the testing chamber 108 and may include a commercially-available pyrolysis probe and platinum resistance coil capable of heating the sample at a constant heating rate in the range of $\beta=20 \times 10^{-3}$ to $20 \times 10^3$ K/s. A computer system-controlled purge gas mass flow controller 118 measures and controls the flow of the purge gas through purge gas inlet 114 into the heated tested chamber 108 to provide an anaerobic pyrolysis environment.

Combustion furnace portion 106 is preferably an ultra-high temperature combustion furnace capable of providing flame-equivalent temperatures (i.e., 1200-1800° C.). Combustion furnace portion 106 preferably has an upper temperature greater than 1200° C. and preferably in the range 1500-1800° C. and, in one embodiment, has an upper temperature of 1600° C. In one embodiment, heating member 120 of combustion furnace portion 106 includes a coil of high-temperature nickel tubing (i.e. Inconel) contained in a ceramic heater and surrounded by ceramic fiber insulation and a cylindrical aluminum shell.

Mixing section 104 may be configured to receive through an inlet 122 a sufficient and continuous flow of reactive gas (e.g., oxygen) to effect complete combustion (oxidation in the case where oxygen is introduced) of the specimen gases in the combustion furnace portion 106. A computer system-controlled oxygen mass flow controller 124 measures and controls the flow of the oxygen or other reactive gas through inlet 122 and controls the proportion of fuel gases and oxygen in a uniform mixture and at a volumetric flow rate of inert purge gas and oxygen, where the combined total of the inert purge gas volumetric flow rate and the oxygen volumetric flow rate is constant.

In one embodiment of the MFC, the pyrolyzer portion 102, mixing section 104, and combustion furnace portion 106 are integrated into one device. For example, the pyrolyzer portion 102 and combustion furnace portion 106 may be contiguous sections of a single ceramic tube 126 with mixing portion 104 comprising a small region (e.g., approximately 1 cm.) between pyrolyzer portion 102 and combustion furnace portion 106 such as shown in FIG. 1. Such design has been shown to improve results by preventing condensation of high molecular-weight pyrolysis products on the walls of the ceramic tube 126 because as the temperature gradients of pyrolyzer portion 102 and combustion furnace portion 106 overlap during sample heating, the mixing portion 104 is always at a temperature that is higher than the temperature of the pyrolyzer portion 102. However, it is within the scope of the techniques disclosed herein to include an MFC 100 having a separate combustion furnace that is coupled with a pyrolyzer furnace, such as a commercially available thermogravimetric analyzer (TGA) or similar device capable of pyrolyzing specimens.

Figure 2:
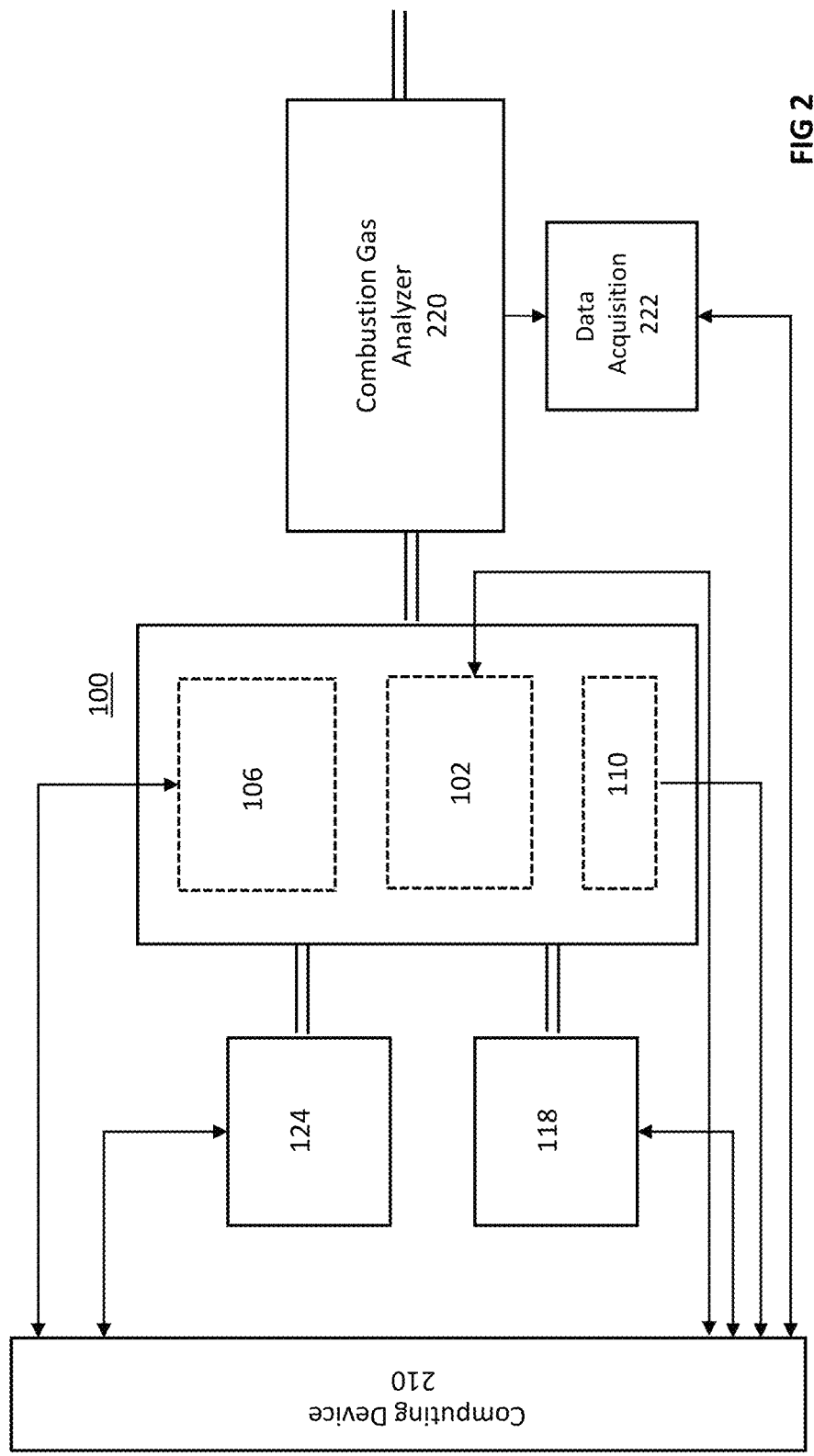
FIG. 2 is a diagram showing aspects and features of an exemplary microscale fire calorimeter (MFC) system for generating combustion products including soot.

Operation of one embodiment may be understood with additional reference to FIG. 2. A specimen to be tested by the MFC 100 is placed in sample cup 112 in testing chamber 108 of pyrolyzer portion 102. Computing device 210 controls purge gas mass flow controller 118 to introduce the purge gas into test chamber 108 via purge gas inlet 114 and controls heating member 116 to incrementally increase the temperature at a constant rate in testing chamber 108; computing device 210 further continually monitoring the testing chamber 108 temperature via temperature sensor 110 as the specimen reaches its temperature of thermal decomposition temperature, and chemically breaks down into gaseous (pyrolyzate) and solid (i.e., char and ash) components.

The pyrolyzate and other products resulting from this pyrolysis are swept out of the testing chamber 108, where they are mixed in mixing section 104 with oxygen via inlet 122 and oxygen mass flow controller 124, which is also controlled by computing device 210. Computing device 210 is configured to control purge gas mass flow controller 118 and oxygen mass flow controller 124 to provide in testing chamber 108 a pre-mixed (uniform) volume of the generated fuel gases (pyrolyzate) and oxygen at precise, prescribed, local equivalence ratios, $\phi$, and at specimen pyrolysis temperatures throughout the MCC test (discussed in more detail below). It will be understood that while oxygen is generally used, any reactive oxidizer (for example nitrous oxide ($NO_2$) or carbon monoxide (CO)) may be used.

Combustion furnace portion 106 combusts the resulting pre-mixed volume of the generated fuel gases (pyrolyzate) and oxygen from mixing section 104 at temperatures typical of flame temperatures using a non-flaming combustion process (i.e., thermal combustion) in order to produce combustion products (in gas stream 121) for analysis. Computing device 210 is further configured to precisely control the heating element 120 to maintain a constant temperature of the combustion furnace portion 106 at greater than 1200° C. and, in one embodiment, at least 1600° C.

After combustion, the combustion products may be provided to combustion gas analyzer 220 for analysis. In one embodiment shown in FIG. 3, combustion gas analyzer 220 includes gas filter 318, multi-gas analyzer 310, a gas conditioning unit 312, a flow meter 314, and an oxygen sensor/analyzer 316).

Figure 3:
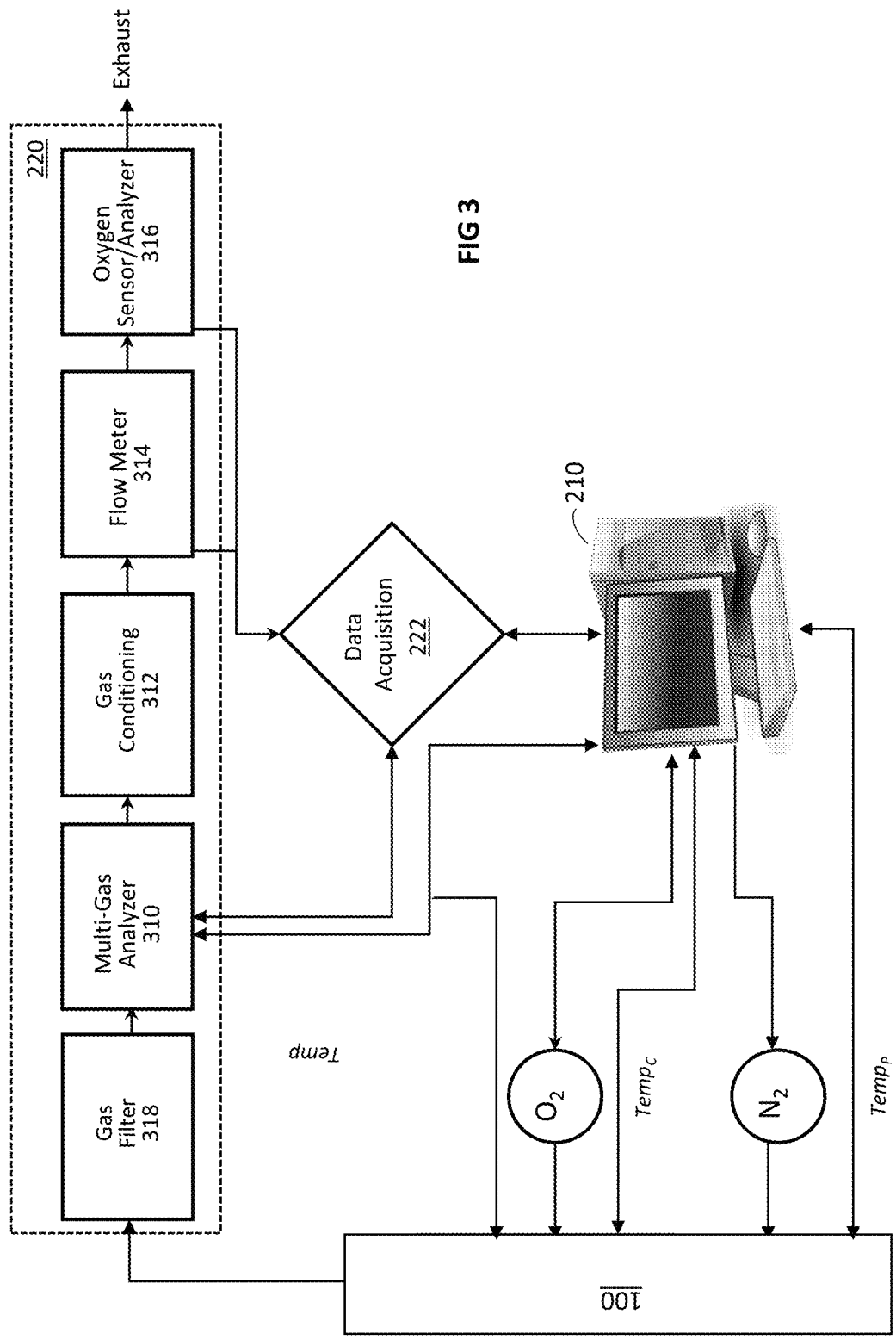
FIG. 3 is a diagram showing further aspects and features of an exemplary microscale fire calorimeter (MFC) system for generating combustion products including soot.

In some embodiments, for example during acid gas analysis, the gas stream 121 exiting MFC 100 must be kept at a high enough temperature to prevent condensation of water and the resulting loss of the acids. In one embodiment, the gas stream 121 should not fall below 150° C. to prevent the loss of acid analyte on moist tubing surfaces. As shown in FIG. 3, the gas stream 121 exiting MFC 100 is provided to an oven-heated gas filter 318, which operates to collect condensable tars and solids. In one embodiment, gas filter 318 is composed of two sandwiched filters: A 1 micron glass and 0.2 micron 25 mm polytetrafluoroethylene (PTFE) filters in a stainless steel filter housing. Heating after combustion furnace portion 106 and prior to gas filter 318 is set to a temperature to ensure the gas stream 121 entering the filter 318 is within the same heating tolerances as the gas filter oven (not shown). In one embodiment, the gas filter 318 oven is preferably controlled to a temperature of 150° C. to no greater than 165° C.

Multi-gas analyzer 310 is configured to measure the type and amount of combustion products from combustion furnace portion 106 and is maintained at temperatures sufficient to prevent condensation of gases to liquids in the combustion stream. In one embodiment (FIG. 3), multi-gas analyzer 310 receives the gases that are the byproducts of the combustion prior to scrubbing in gas conditioning unit 312. In one embodiment, multi-gas analyzer 310 is an infrared spectrometer multi-gas analyzer, such as a Fourier-transform infrared (FTIR) spectrometer, with a post-filter sample line and a gas sample cell (not shown) maintained at 170° C. In that embodiment, the temperature of the heating after combustion furnace portion 106 and prior to gas filter 318 is at least 5 degrees Celsius lower than the FTIR's sample cell in order to trap condensable tars that would otherwise condense on the FTIR gas cell's optics.

In further aspects and features of the MFC devices and techniques, additional in-line analyzing techniques, such as dedicated gas analyzers may be included or gases may be collected for off-line chemical analysis. For example, instrumentation including, but not limited to, carbon monoxide (CO) and carbon dioxide ($CO_2$) sensors, hydrocarbon analyzers, other electrochemical gas sensors, and mass spectrometer (MS) can be attached to evaluate the gases as a function of heating rate, flow rate and combustion temperature. This enables the on-line evaluation and quantification of decomposition products. However, while such dedicated gas analyzers and collectors can be used to measure some combustion products such as carbon monoxide, carbon dioxide, total hydrocarbons, water, halogen acids and selected gases, they are unable to measure all of these simultaneously during the test. Corrosive and condensable products in the combustion stream (which include some of the more toxic combustion products) must be removed prior to the reaching some of these analyzers).

Gas conditioning unit 312 may remove ("scrub") gases that are the byproducts of the combustion including condensed phase char, condensed tars, gas phase $CO_2$, and acid gases (e.g. HCl, HBr, HF, $H_2SO_4$, $H_3PO_4$), and/or $H_2O$. The flow rate downstream of the gas conditioning unit 312 is measured by mass flow meter 314 and any remaining oxygen gas may be measured at the oxygen sensor 316. In one embodiment, $H_2O$ is not removed prior to gas measurement.

A data acquisition system 222 may detect and measure various data and information resulting from the test including, but not limited to, data from multi-gas analyzer 310, mass flow meter 314, and oxygen sensor 316. In one embodiment, data acquisition device 222 is implemented as a sensor to measure data from multi-gas analyzer 310, mass flow meter 314, and oxygen sensor/analyzer 316, and a multi-channel data acquisition device (including signal conditioning and A/D converter for converting the data from multi-gas analyzer 310, mass flow meter 314, and oxygen sensor 316) in communication with software executing on and controlled by computing device 210. In one embodiment, data acquisition system 222 is a system commercially available from National Instruments.

Figure 4:
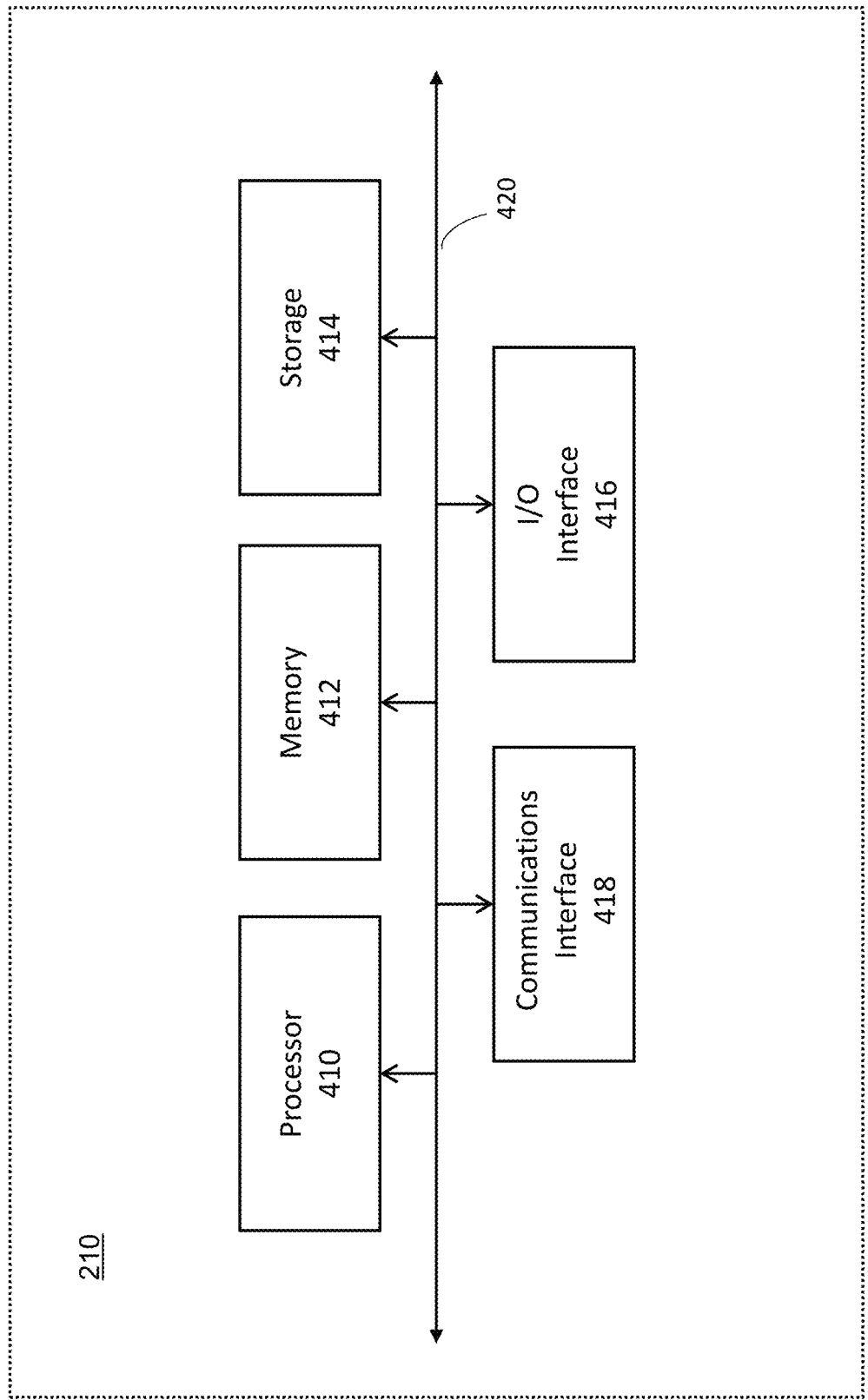
FIG. 4 is a block diagram showing an exemplary computing system for use with one embodiment of microscale fire calorimeter (MFC) system.

In one embodiment, data acquisition system 222 is communicatively coupleable to and controlled by computing device 210. FIG. 4 is a block diagram of an exemplary embodiment and components of computing device 210 and, in one embodiment may be a personal computer. As shown in FIG. 4, computing device 210 may include a processor 410, a memory 412, storage 414, I/O interface 416, a communication interface 418, and internal bus architecture 420.

Processor 410 may be a general-purpose microprocessor (e.g., a central processing unit (CPU), a graphics processing unit (GPU), a microcontroller, a microprocessor, a digital signal processor (DSP), an application specific integrated circuit (ASIC), a field programmable gate array (FPGA), a programmable logic device (PLD), a controller, a state machine, gated or transistor logic, discrete hardware components, or any other suitable entity or combinations thereof that can perform calculations, process instructions for execution, and/or other manipulations of information. In some implementations, processor 410 includes one or more multiple processors capable of being programmed to perform a function; for example, processor 410 may be programmed to receive data and information from and/or provide data and information to data acquisition system 222 and others devices including pyrolyzer portion 102, combustion furnace portion 106, temperature sensor 110, purge gas mass flow controller 118, oxygen mass flow controller 124, and combustion gas analyzer 220. Processor 410 may be implemented in hardware, firmware, or a combination of hardware and software.

Memory 412 may include read only memory (ROM), cache, random access memory (RAM), and/or another type of dynamic or static storage (e.g., a flash memory, a magnetic memory, and/or an optical memory) that stores information and/or instructions for use by processor 410. In one embodiment, memory 412 is configured to store programmable software of data acquisition system 222.

Storage 414 stores information and/or software related to the operation and use of computing device 210 and may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

The I/O interface 416 allows a user to provide input to, receive output from, and otherwise transfer data to and receive data from computing device 210. The I/O interface 416 may include a mouse, a keypad or a keyboard, a touchscreen, a camera, an optical scanner, network interface, modem, other known I/O devices or a combination of such I/O interfaces. The I/O interface 416 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 416 is configured to provide graphical data to a display for presentation to a user. The graphical data may be representative of one or more graphical user interfaces and/or any other graphical content as may serve a particular implementation.

Communication interface 418 includes a transceiver and/or a separate receiver and transmitter and may be implemented via a wired connection, a wireless connection, or a combination of wired and wireless connections, including an Ethernet interface, an optical interface, a coaxial interface, an infrared interface, a radio frequency (RF) interface, a universal serial bus (USB) interface, a Wi-Fi interface, a wireless network interface, or the like. Communication interface 418 enables computing device 210 to communicate with other devices, to receive data and information from and/or to provide data and information to another device, including pyrolyzer portion 102, combustion furnace portion 106, temperature sensor 110, purge gas mass flow controller 118, oxygen mass flow controller 124, and combustion gas analyzer 220, and any non-software components of data acquisition device 222.

Internal bus architecture 420 may include hardware, software, or both that communicatively couples components of the computing device 212 to each other and may include data buses, address buses, and control buses. As an example and not by way of limitation, internal bus architecture 420 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

Computing device 210 may perform one or more processes described herein and may perform these processes based on processor 410 executing software instructions stored by a non-transitory computer-readable medium, such as memory 412 and/or storage 414. Software instructions may be read into memory 412 and/or storage 414 from another computer-readable medium or from another device via communication interface 418. When executed, software instructions stored in memory 412 and/or storage 414 may cause processor 410 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 4 are provided exemplary only. Computing device 210 may include additional components, fewer components, different components, or differently arranged components than those shown in FIG. 4. Additionally, or alternatively, a set of components (e.g., one or more components) of computing device 210 may perform one or more functions described as being performed by another set of components of computing device 210.

Computing device 210 may be operatively coupled to heating elements 116 of pyrolyzer portion 102 and heating element 120 of combustion furnace portion 106 as well as purge gas mass flow controller 118 and oxygen mass flow controller 124 to control the mixture of the generated fuel gases with oxygen at local and precise constant equivalence ratios $$\Phi = r_0(T)/r(T)$$

where $r(T)$ is the oxygen/fuel mass ratio at each sample temperature T during the test, and $r_0(T)$ is the oxygen/fuel mass ratio at these temperatures for complete (stoichiometric) combustion of the fuel gases, in order to produce a premixed (uniform) mixture of fuel and oxygen for combustion at high heat in the combustion furnace portion 106. More details on this process will be understood with reference to FIG. 5.

Figure 5:
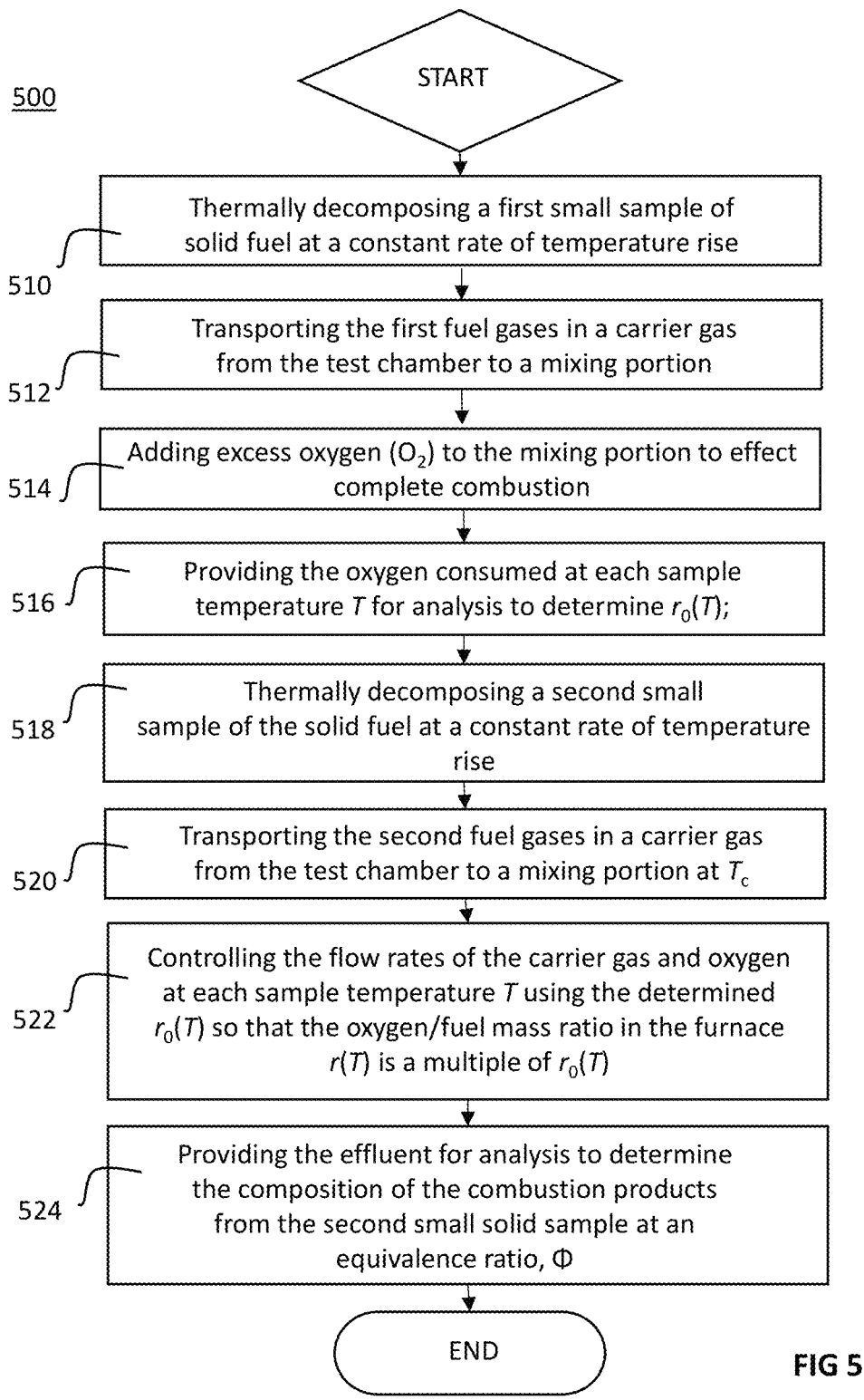
FIG. 5 is a flow diagram showing an exemplary microscale fire calorimeter (MFC) process for generating combustion products including soot; and, FIG. 6 is a graph showing yields of carbon monoxide and hydrogen cyanide vs. equivalence ratio for KEVLAR® polyaramid fiber using an embodiment of the microscale fire calorimeter (MFC) devices and techniques.

FIG. 5 sets forth an exemplary process for generating and determining combustion products including soot using an embodiment of the MFC 100. A small specimen, or sample, of solid material is thermally decomposed at a constant rate of temperature rise, $\beta$, to generate fuel gases in a test chamber; e.g. test chamber 108 (block 510). The generated fuel gases (pyrolyzate) and other products are then transported from the test chamber via carrier gas (e.g., nitrogen) to a mixing portion (block 512) where excess oxygen is then added to effect complete combustion of the fuel gases in a combustion furnace (block 514) (e.g., the generated fuel gases (pyrolyzate) and other products are swept from test chamber 108 via nitrogen introduced via purge gas inlet 114 and purge gas mass flow controller 118 to mixing portion 104 where excess oxygen is then added via to inlet 122 and oxygen mass flow controller 124 to effect complete combustion of the fuel gases in a combustion furnace portion 106).

The oxygen consumed in the furnace is measured by an oxygen analyzer (e.g., oxygen sensor/analyzer 316) at constant combustion furnace temperature $T_c > 1200°$ C. and at each sample temperature, T, during the heating of a first specimen of solid material to determine the mass of oxygen, $\Delta m_{O_2}$ consumed by complete combustion per unit mass, m, of material. In one embodiment, computing device 210 controls data acquisition system 222 to measure the consumed oxygen (block 516) and further calculates the stoichiometric oxygen-to-fuel mass ratio of the material, $r_0(T)$, where:

$$r_0(T) = \Delta m_{O_2}/m$$

and, more specifically, in the case of the combustion of first specimen mass, $m_1$:

$$r_{01}(T) = \Delta m_{O_2}/m_1$$

In one embodiment, this data is stored in memory 412 in computing device 210 (not shown in FIG. 5). More specifically, $\Delta m_{O_2}$ for complete combustion of first specimen mass, $m_1$, may be stored as $\Delta m_{O_2}/m_1$ along with transient sample temperature, T, in a look-up table in memory 412 of computing device 210.

At block 518 a second specimen of the same solid material is inserted into the test chamber (e.g., test chamber 108) and thermally decomposed at a constant rate of temperature rise. As with the first specimen, the fuel gases (pyrolyzate) and other products generated by the thermal decomposition of this second sample of mass, $m_2$, are then transported from the test chamber (e.g. test chamber 108) to a mixing portion in a carrier gas (e.g., mixing portion 104 in nitrogen)(block 520) for combustion in a combustion furnace having temperature $T_c$>1200° C. and, in one embodiment, having a $T_c$=1600° C. In one embodiment, the carrier gas is nitrogen ($N_2$) and computing device 210 controls the total flow rate of $N_2$ at 100 cc/min throughout the test.

The previously determined $r_{01}$ (T) from the test of the first sample of mass, $m_1$ (block 516) is then used to control the proportion of carrier gas and oxygen entering the furnace at a constant total flow rate and at each sample temperature, T, such that the oxygen/fuel mass ratio, r(T), in the furnace at temperature $T_c$, is some multiplier (i.e., fraction or multiple) of $r_0$(T) (block 522). In particular:

$r(T)=r_0(T)/\Phi$, which may alternately be expressed as:

$r(T)=(m_1/m_2)r_{01}(T)/\Phi$.

As is known, $\phi$ is the fuel/oxygen mass ratio relative to the fuel/oxygen mass ratio for complete (stoichiometric) combustion. More specifically, $\phi$ may be expressed as:

$\phi=(m/m_{O2})/(m/\Delta m_{o2})$ where m is the mass of fuel and $m_{O2}$ is the mass of oxygen present at the time of combustion, and $\Delta m_{O2}$ is the mass of oxygen required for complete (stoichiometric) combustion of fuel mass m. Thus it will be appreciated from the above that $\phi$ may also be expressed as:

$\phi=\Delta m_{O2}/m_{O2}$.

In one embodiment, computing device 210 uses information stored in memory 412 to control purge gas mass flow controller 118 and oxygen mass flow controller 124 according to the equation:

$r(T)=r_0(T)/\Phi=(m_1/m_2)r_{01}(T)/\Phi$.

More specifically, the previously-stored $\Delta m_{O_2}/m_1$ and Tare retrieved from memory 412 of computing device 210 during the test to control the oxygen/specimen mass ratio in the combustion furnace portion 106 according to the equation:

$r(T)=r_0(T)/\Phi=(m_1/m_2)r_{01}(T)/\Phi$.

Finally, the gaseous effluent 121 from the combustion furnace (e.g., combustion furnace portion 106) is analyzed to determine the composition of the combustion products from the second sample of material at an equivalence ratio, $\Phi$(e.g., by multi-gas analyzer 310). In one embodiment, the analyzer is an infrared spectrometer multi-gas analyzer such as a Fourier-transform infrared (FTIR) spectrometer with post-filter transfer lines and a sample cell maintained at 170° C.

It was unexpectedly found that, through the microscale fire calorimeter (MFC) device and techniques disclosed herein, the flameless premixed combustion of fuel and oxygen at $T_c$>1200° C. resulted in the production of soot in equilibrium with other incomplete combustion products (including toxic gases), which would change in type and amount with the change in fuel/oxygen ratio and combustor temperature, similar to what occurs in diffusion flames/fires over the normal range of fire conditions.

Figure 6:
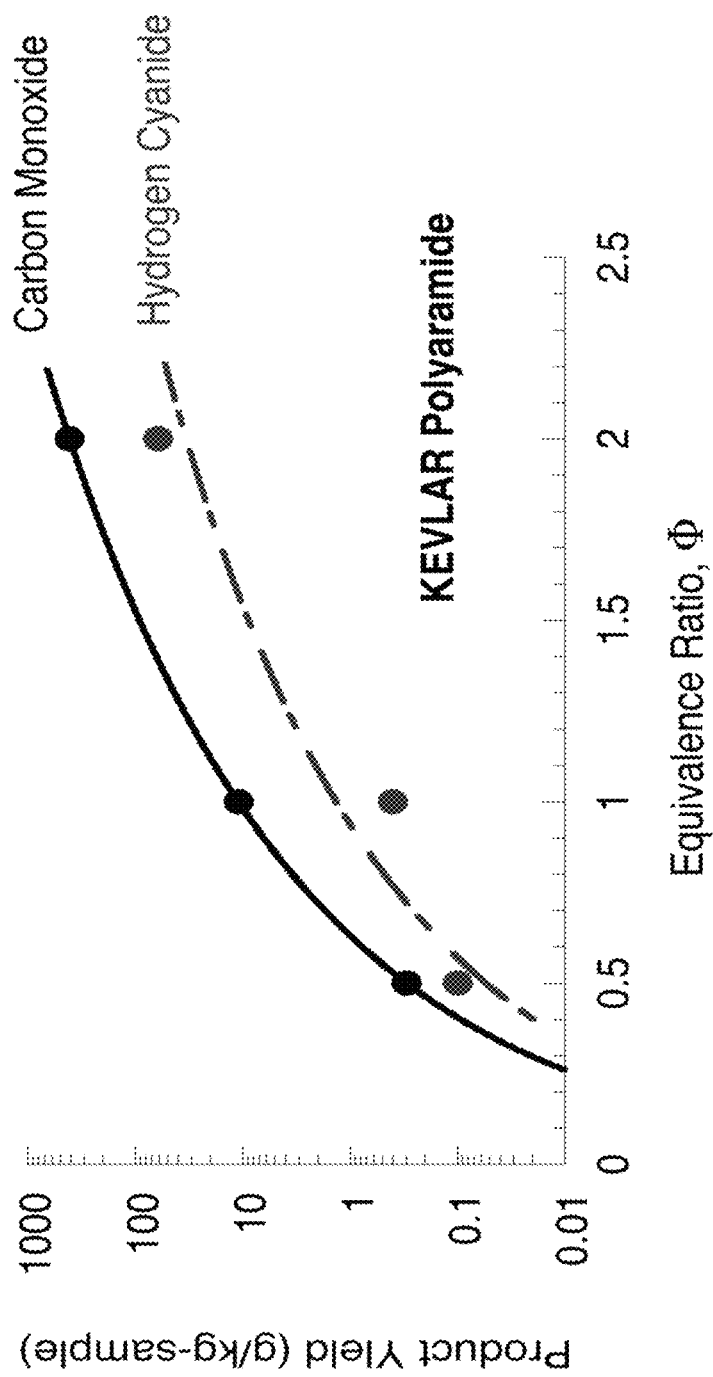

Several polymers were tested at constant equivalence ratios $\Phi$ ranging from $\Phi$=0.5 (fuel lean) to 2.0 (fuel rich) in a fifteen-minute test and at combustion temperatures ranging from Tc=750-1500° C. The yields of CO, $CO_2$, $H_2O$, $NO_2$, NO, $N_2O$, HCN, $SO_2$, COS, $CS_2$, $CH_4$, $C_2H_2$, $C_2H_4$, $C_2H_6$, $C_3H_8$ and $C_6H_5OH$ were determined over this range. An example of the yield from the microscale fire calorimeter (MFC) devices and techniques disclosed herein may be seen in FIG. 6. More particularly, FIG. 6 is a graph showing the mass of carbon monoxide and hydrogen cyanide produced per unit specimen mass (yield) vs. equivalence ratio for KEVLAR® polyaramid fiber. FIG. 6 shows that the amount of toxic carbon monoxide and hydrogen cyanide gases increases exponentially with $\Phi$, as would occur during the later stages of a fire involving KEVLAR® materials when oxygen becomes depleted. Thus the MFC devices and techniques disclosed herein allowed for the generation and measurement of the type and nature of combustion products in a diffusion flame over a full range of fire stages.

The MFC devices and techniques disclosed herein use milligram-sized solid fuel samples to generate solid fuel gases, which are then mixed with oxygen under controlled conditions to obtain precise fuel/oxygen ratios throughout a test and then combusted under flameless, premixed (uniform) conditions. The ability of the MFC devices and techniques disclosed herein to generate soot in premixed combustion of fuel gases from thermally decomposed solids at high combustor temperatures and high fuel/oxygen ratios relative to stoichiometric fuel oxygen ratios opens the possibility for real "fire like conditions" with regard to combustion products in a microscale test. The MFC devices and techniques allow for the generation and analyses of combustion products of burning materials at each stage of fire growth—from early stage fires where oxygen is in excess ($\Phi$<1) to late-stage fires burning in air that is oxygen depleted ($\Phi$>1), thus making the embodiments disclosed herein useful for safety research, quality control, fundamental combustion studies, and for screening materials and products for fire toxicity).

Although a few example implementations have been described in detail above, these should not be construed as limitations on the scope of what may be claimed, but rather as descriptions of features that may be specific to particular embodiments. Thus, other modifications and embodiments are possible and are within the scope of the appended claims and equivalents thereof. For example, the MFC devices and techniques set forth in the drawings show a device wherein the pyrolyzer portion, mixing and combustion furnace portion are integrated in one unit. However, it is within the scope of the techniques disclosed herein to include a device having a separate combustion furnace component coupleable to a separate pyrolyzer furnace component such as a thermogravimetric analyzer (TGA). Further, in addition to the components of combustion gas analyzer 220 disclosed herein, additional analyzers including carbon monoxide (CO) and carbon dioxide ($CO_2$) sensors, hydrocarbon analyzers, electrochemical gas analyzers, and mass spectrometer (MS) may be added to provide additional testing data and information. Further, as known, various other devices can be attached to evaluate the pyrolysis gases as a function of heating rate, flow rate, and combustion temperature. This enables the on-line evaluation and quantification of decomposition products. In addition the foregoing, it will also be understood that the logic flows and actions recited in the depicted figures and recited in the claims do not require the particular order shown, or in sequential order claimed, and may be performed in a different order and still achieve desirable results.

No language in the specification should be construed as indicating any non-claimed element as essential to the practice of the techniques of this disclosure. The terms "a"

and "an" are used interchangeably above, and are equivalent to the phrase "one or more" as utilized in the present application. The terms "comprising," "having," "including," and "containing" are to be construed as open-ended terms (i.e., meaning "including, but not limited to,") unless otherwise noted above. The recitation of any ranges of values herein is merely intended to serve as a shorthand technique of referring individually to each separate value falling within the range, unless otherwise indicated herein, and each separate value is incorporated into the specification as if it were individually recited. The use of any and all examples, or example language (e.g., "such as"), provided herein is intended merely to better illuminate the disclosure and does not impose a limitation on the scope of the disclosure unless otherwise claimed. Finally, any papers and publications cited herein are hereby incorporated by reference in their entirety.

What is claimed is:

1. A microscale fire calorimeter system for determining the products of pre-mixed combustion of milligram-sized samples of solid materials at flame temperatures and across a range of fuel/oxygen ratios, comprising:
    a pyrolyzer including a heating member for thermally decomposing a milligram-sized sample of a solid material under anaerobic conditions to generate fuel gases, the pyrolyzer including an inlet for receiving a purge gas and a mass flow controller for controlling the mass flow rate of the purge gas through the purge gas inlet into the pyrolyzer;
    a mixing portion for generating a premixed volume of the generated fuel gases and oxygen, the mixing portion including an inlet for receiving oxygen and a mass flow controller for controlling the volumetric flow rate of the oxygen through the oxygen inlet into the mixing portion; and,
    an ultra-high temperature combustion furnace including a heating member for combusting the premixed volume of the generated fuel gases and oxygen at flame temperatures in order to produce gaseous and solid combustion products;
    wherein the purge gas mass flow controller and the oxygen mass flow controller are configured to receive computer instructions through at least one computer interface, the computer instructions for controlling the purge gas mass flow controller and the oxygen mass flow controller to create a constant total volumetric flow rate of oxygen and inert purge gas and for controlling the purge gas mass flow controller and the oxygen mass flow controller so that the oxygen-to-fuel mass ratio, r(T), in the ultra-high temperature combustion furnace at each temperature, T, is a multiplier of $r_0(T)$, wherein $r_0(T)$ is the stoichiometric oxygen-to-fuel mass ratio for complete combustion of the solid material at the temperature, T.

2. The microscale fire calorimeter system of claim 1, wherein the ultra-high temperature combustion furnace is capable of maintaining temperatures in the range of 1200 to 1800 degrees Celsius.

3. The microscale fire calorimeter system of claim 1, further comprising multi-gas analyzer means configured to receive the gaseous and solid combustion products from the ultra-high temperature combustion furnace and capable of measuring the type and amount of the gaseous and solid combustion products.

4. The microscale fire calorimeter system of claim 3, wherein the multi-gas analyzer means includes a Fourier-transform infrared (FTIR) spectrometer including a sample cell controlled to maintain a minimum temperature in order to prevent the loss of the gaseous combustion products by condensation.

5. The microscale fire calorimeter system of claim 4, wherein the sample cell minimum temperature is 170 degrees Celsius.

6. The apparatus of claim 1, wherein the milligram-sized sample of solid material is a plastic.

7. The apparatus of claim 6, wherein the plastic is flame retardant.

8. A method for determining the products of pre-mixed combustion of a milligram-sized sample of solid material at flame temperatures and across a range of fuel/oxygen ratios using a microscale fire calorimeter system, comprising the steps of:
    in a pyrolyzer of the microscale fire calorimeter system, thermally decomposing a milligram-sized sample of a solid material under anaerobic conditions to generate fuel gases, the pyrolyzer including an inlet for receiving a purge gas and a mass flow controller for controlling the mass flow rate of the purge gas through the purge gas inlet into the pyrolyzer;
    in a mixing portion of the microscale fire calorimeter system, generating a premixed volume of the generated fuel gases and oxygen, the mixing portion including an inlet for receiving oxygen and a mass flow controller for controlling the volumetric flow rate of the oxygen through the oxygen inlet into the mixing portion;
    in an ultra-high temperature combustion furnace of the microscale fire calorimeter system, combusting the premixed volume of the generated fuel gases and oxygen at flame temperatures in order to produce gaseous and solid combustion products;
    controlling the purge gas mass flow controller and the oxygen mass flow controller to create a constant total volumetric flow rate of oxygen and inert purge gas; and,
    controlling the purge gas mass flow controller and the oxygen mass flow controller so that the oxygen-to-fuel mass ratio, r(T), in the ultra-high temperature combustion furnace at each temperature, T, is a multiplier of $r_0(T)$, wherein $r_0(T)$ is the stoichiometric oxygen-to-fuel mass ratio for complete combustion of the solid material at the temperature, T.

9. The method of claim 8, wherein the ultra-high temperature combustion furnace is capable of maintaining temperatures in the range of 1200 to 1800 degrees Celsius.

10. The method of claim 8, further comprising the step of:
    measuring the type and amount of the gaseous and solid combustion products using multi-gas analyzer means configured to receive the gaseous and solid combustion products from the ultra-high temperature combustion furnace.

11. The method of claim 10, wherein the multi-gas analyzer means includes a Fourier-transform infrared (FTIR) spectrometer including a sample cell, further comprising the step of:
    controlling the sample cell to maintain a minimum temperature in order to prevent the loss of the gaseous combustion products by condensation.

12. The method of claim 11, wherein the sample cell minimum temperature is 170 degrees Celsius.

13. The method of claim 8, wherein the milligram-sized sample of solid material is a plastic.

14. The method of claim 13, wherein the plastic is treated with at least one flame retardant chemical.

15. A microscale fire calorimeter system for determining the products of pre-mixed combustion of milligram-sized samples of solid materials at flame temperatures and across a range of fuel/oxygen ratios, comprising:
  pyrolysis means for thermally decomposing a milligram-sized sample of a solid material under anaerobic conditions to generate fuel gases, the pyrolysis means configured to receive a purge gas and including purge gas mass flow controller means for controlling the mass flow rate of the purge gas into the pyrolysis means;
  an ultra-high temperature combustion furnace including:
    a mixing portion for generating a premixed volume of the generated fuel gases and oxygen, the mixing portion configured to receive the oxygen and including oxygen mass flow controller means for controlling the volumetric flow rate of the oxygen through into the mixing portion; and,
    a heating member for combusting the premixed volume of the generated fuel gases and oxygen at flame temperatures in order to produce gaseous and solid combustion products;
  at least one computer interface configured to receive computer instructions for controlling the purge gas mass flow controller means and the oxygen mass flow so that the total volumetric flow rate of oxygen and inert purge gas is constant and so that the oxygen-to-fuel mass ratio, $r(T)$, in the ultra-high temperature combustion furnace at any temperature, T, is a multiplier of $r_0(T)$, wherein $r_0(T)$ is the stoichiometric oxygen-to-fuel mass ratio for complete combustion of the solid material at the temperature, T.

16. The microscale fire calorimeter system of claim 15, wherein the ultra-high temperature combustion furnace is capable of maintaining temperatures in the range of 1200 to 1800 degrees Celsius.

17. The microscale fire calorimeter system of claim 15, further comprising:
  multi-gas analyzer means configured to receive the gaseous and solid combustion products from the ultra-high temperature combustion furnace and capable of measuring the type and amount of the gaseous and solid combustion products, wherein the multi-gas analyzer means includes a Fourier-transform infrared (FTIR) spectrometer including a sample cell controlled to maintain a minimum temperature in order to prevent the loss of the gaseous combustion products by condensation.

18. The method of claim 15, wherein the milligram-sized sample of solid materials is a plastic treated with at least one flame retardant chemical.

* * * * *